(12) United States Patent
Zur Nieden

(10) Patent No.: US 9,958,319 B2
(45) Date of Patent: May 1, 2018

(54) METHOD AND DEVICE FOR DETERMINING A CRITICAL ANGLE OF AN EXCITATION LIGHT BEAM

(71) Applicant: Carl Zeiss Microscopy GmbH, Jena (DE)

(72) Inventor: Robin Zur Nieden, Goettingen (DE)

(73) Assignee: Carl Zeiss Microscopy GmbH (DE)

( * ) Notice: Subject to any disclaimer, the term of this patent is extended or adjusted under 35 U.S.C. 154(b) by 298 days.

(21) Appl. No.: 13/857,610

(22) Filed: Apr. 5, 2013

(65) Prior Publication Data

US 2013/0265407 A1    Oct. 10, 2013

(30) Foreign Application Priority Data

Apr. 5, 2012   (DE) ........................ 10 2012 102 983

(51) Int. Cl.
*G01N 21/64* (2006.01)
*G01J 1/58* (2006.01)
*G02B 21/16* (2006.01)

(52) U.S. Cl.
CPC ............ *G01J 1/58* (2013.01); *G01N 21/6458* (2013.01); *G02B 21/16* (2013.01)

(58) Field of Classification Search
CPC .. G01N 21/6458; G01N 21/648; G01N 21/64; G12B 13/00
(Continued)

(56) References Cited

U.S. PATENT DOCUMENTS 4,640,616 A * 2/1987 Michalik ....................... 356/136
5,313,264 A   5/1994 Ivarsson et al.
(Continued)

FOREIGN PATENT DOCUMENTS

DE   10350747    10/2003
DE   69926908 T2  6/2006
(Continued)

OTHER PUBLICATIONS

Martin Oheim et al., "Topical Review; Non-linear evanescent-field imaging", Journal of Physics D: Applied Physics, Institute of Physics Publishing Ltd., GB, vol. 38, No. 10, May 21, 2005 (May 21, 2005), pp. R185-R197.
(Continued)

*Primary Examiner* — Gims Philippe
*Assistant Examiner* — Albert Kir
(74) *Attorney, Agent, or Firm* — Mayback & Hoffman, P.A.; Gregory L. Mayback; Rebecca A. Tie

(57) ABSTRACT

A method for determining a critical angle of total reflection based upon images captured at different angles of incidence of a light beam includes illuminating a sample with an excitation light beam, capturing images of at least part of the sample at a plurality of different angles of incidence of the excitation light beam, and determining a critical angle of total reflection at an interface of the sample based upon analysis of the images. An apparatus for determining a critical angle of total reflection at an interface of a sample includes a light source arrangement to illuminate a sample with an angle of incidence, an image capturing arrangement to capture an image of the sample, and a processing arrangement to determine the critical angle of total reflection at an interface of the sample on the basis of an analysis of images captured at a plurality of different angles of incidence.

22 Claims, 3 Drawing Sheets

(58) Field of Classification Search
USPC .... 348/79, 46; 356/445, 318, 246, 326, 135, 356/128, 136; 250/459, 458, 461, 453, 250/252.1, 461.2
See application file for complete search history.

(56) References Cited

U.S. PATENT DOCUMENTS

| | | | |
|---|---|---|---|
| 5,987,991 A * | 11/1999 | Trantow et al. | 73/624 |
| 6,097,479 A * | 8/2000 | Melendez et al. | 356/136 |
| 6,843,963 B1 | 1/2005 | Jennissen | |
| 7,391,565 B2 * | 6/2008 | Lauer | 359/368 |
| 9,012,872 B1 * | 4/2015 | Fang | G01N 21/648 250/461.2 |
| 2001/0018184 A1 | 8/2001 | Williams | |
| 2002/0097489 A1 * | 7/2002 | Kawano et al. | 359/388 |
| 2003/0011768 A1 * | 1/2003 | Jung et al. | 356/326 |
| 2004/0075827 A1 * | 4/2004 | Byrne | 356/128 |
| 2004/0174523 A1 * | 9/2004 | Uhl et al. | 356/318 |
| 2004/0196457 A1 * | 10/2004 | Aono et al. | 356/318 |
| 2005/0051733 A1 * | 3/2005 | Wiki et al. | 250/453.11 |
| 2005/0092934 A1 * | 5/2005 | Kang et al. | 250/458.1 |
| 2005/0179903 A1 * | 8/2005 | Tsuruta et al. | 356/445 |
| 2006/0012784 A1 * | 1/2006 | Ulmer | 356/246 |
| 2006/0012793 A1 * | 1/2006 | Harris | 356/436 |
| 2007/0035821 A1 * | 2/2007 | Hecker | 359/385 |
| 2007/0052958 A1 * | 3/2007 | Ulrich et al. | 356/318 |
| 2007/0097496 A1 | 5/2007 | Ulrich | |
| 2007/0097497 A1 * | 5/2007 | Thirase et al. | 359/385 |
| 2007/0153373 A1 | 7/2007 | Uhl | |
| 2009/0092970 A1 | 4/2009 | Williams | |
| 2009/0168158 A1 * | 7/2009 | Schwertner et al. | 359/385 |
| 2010/0093068 A1 | 4/2010 | Williams | |
| 2011/0057093 A1 * | 3/2011 | Gonschor | G01N 21/6458 250/252.1 |
| 2011/0121204 A1 * | 5/2011 | Kumazaki et al. | 250/459.1 |
| 2011/0275523 A1 | 11/2011 | Quake | |
| 2011/0278476 A1 * | 11/2011 | Chen et al. | 250/461.1 |
| 2012/0002031 A1 * | 1/2012 | Pertsinidis et al. | 348/79 |
| 2012/0129723 A1 | 5/2012 | Notcovich | |
| 2012/0242981 A1 * | 9/2012 | Wagner | 356/128 |
| 2014/0104601 A1 * | 4/2014 | Baba | 356/135 |

FOREIGN PATENT DOCUMENTS

| | | |
|---|---|---|
| DE | 102006021996 A1 | 2/2007 |
| DE | 102007020610 A1 | 11/2008 |
| DE | 102011000456 A1 | 8/2011 |
| DE | 102010041426 A1 | 5/2012 |
| DE | 112010003414 T5 | 12/2012 |
| EP | 0071143 A1 * | 2/1983 |
| EP | 2439576 A1 * | 4/2012 |
| WO | 2005031429 A1 | 4/2005 |
| WO | 2006048683 A1 | 5/2006 |
| WO | 2008125855 A1 | 10/2008 |
| WO | 2010141122 A1 | 12/2010 |
| WO | 2012051206 A1 | 4/2012 |

OTHER PUBLICATIONS

Office Action from European Patent Office for Application No. 13162345.6 dated Jul. 28, 2017.

* cited by examiner

METHOD AND DEVICE FOR DETERMINING A CRITICAL ANGLE OF AN EXCITATION LIGHT BEAM

CROSS-REFERENCE TO RELATED APPLICATIONS

This application claims the priority, under 35 U.S.C. § § 119 and 371, of German patent application No. DE 10 2012 102 983.0, filed Apr. 5, 2012; the prior application is herewith incorporated by reference in its entirety.

STATEMENT REGARDING FEDERALLY SPONSORED RESEARCH OR DEVELOPMENT

Not Applicable

FIELD OF THE INVENTION

The present application relates to methods and apparatuses for determining a critical angle of total reflection of an excitation light beam in a microscopy arrangement, in particular in TIRF-microscopy arrangements ("Total Internal Reflection Fluorescence").

BACKGROUND OF THE INVENTION

Total internal reflection fluorescence microscopy is a particular measurement method in light microscopy in which an excitation light beam is typically totally reflected at an interface between a cover glass or slide and a sample. This generates a so-called evanescent (decaying) field in the sample which may excite the sample to fluorescence. The penetration depth of the evanescent fields depends on the exact angle of incidence of the excitation light beam.

As the critical angle for total reflection, i.e. the threshold angle at which a transmitted light beam vanishes, depends on the indices of refraction of the materials involved, this angle depending on the type of samples used, may not be known from the start. Therefore, it is desirable to be able to determine the critical angle.

United States Patent Publication No. 2011/0057093 A1 discloses a method evaluating the intensity of an optical response of a sample depending on an angle of incidence of irradiation light. To increase robustness of the method, an analysis is performed in a pupil plane which sometimes requires additional optical elements.

Therefore, a need exists for methods and devices for determining such a critical angle which should be easy to implement, preferably without using additional optical elements, and which are robust.

Thus, a need exists to overcome the problems with the prior art systems, designs, and processes as discussed above.

SUMMARY OF THE INVENTION

According to an embodiment, a method is provided, comprising:
illuminating a sample with an excitation light beam,
capturing images of the sample for a plurality of different angles of incidence of the excitation light beam, and
determining a critical angle of total reflection of the excitation light beams depending on the captured images, i.e. based on the captured images.

Due to such a determination of the critical angle on the basis of the images it is not necessary to view a pupil plane for increasing robustness. Furthermore, the capturing of images in some embodiments may be performed with an image sensor which is provided already for other purposes such that no additional elements are needed.

In an embodiment, the determination of the critical angle may be performed on the basis of a contrast analysis of the images. For this determination it may be used that, when passing the angle of total reflection, contrast ratios, in particular intensity ratios, may change.

In an embodiment, images of different image planes within the sample are captured, for example of two different image planes, and the determining of the critical angle may be performed on the basis of the images of the different image planes, for example by comparing of images at equal angles of incidence and different image planes. In an embodiment, in this way a result may be verified which was obtained on the basis of images of a single image plane.

The method in some embodiments may also comprise a comparing of image parameters, for example a mean captured fluorescence intensity in an area, between successive angles of incidence of the plurality of different angles of incidence. Additionally or alternatively, in embodiments at least in some of the images different areas, for example an area within an evanescent field and an area outside an evanescent field, may be analysed.

A ratio of image intensities may, for example be determined along one or more line profiles, using overall images or predetermined areas of an image.

The method may be performed automatically or semi-automatically. For example a change of the angle of incidence and/or a change of image plane of detection, i.e. image capturing, may be performed automatically, but may also be performed by a user in an interactive manner.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which.

DETAILED DESCRIPTION OF THE INVENTION

In the following, embodiments will be described in detail. These embodiments serve merely illustration purposes and are not to be construed as limiting the scope of the present application. Features of different embodiment may be combined with each other to form further embodiments unless noted otherwise. On the other hand, a description of an embodiment with a plurality of features is not to be construed as indicating that all these features are necessary for practising the invention. In particular, in other embodiments some features of the described embodiments may be omitted and/or replaced by alternative features.

As common in the field of optics an angle of incidence of a light beam in the context of this application indicates the angle between this light beam and a direction perpendicular to a surface of an object through the point of incidence of the light beam on the object. In other words, an angle of incidence of 0° corresponds to a light incidence perpendicular on the illuminated object, while an angle of incidence of 90° corresponds to a glancing incidence parallel to a surface of the object.

Figure 1:
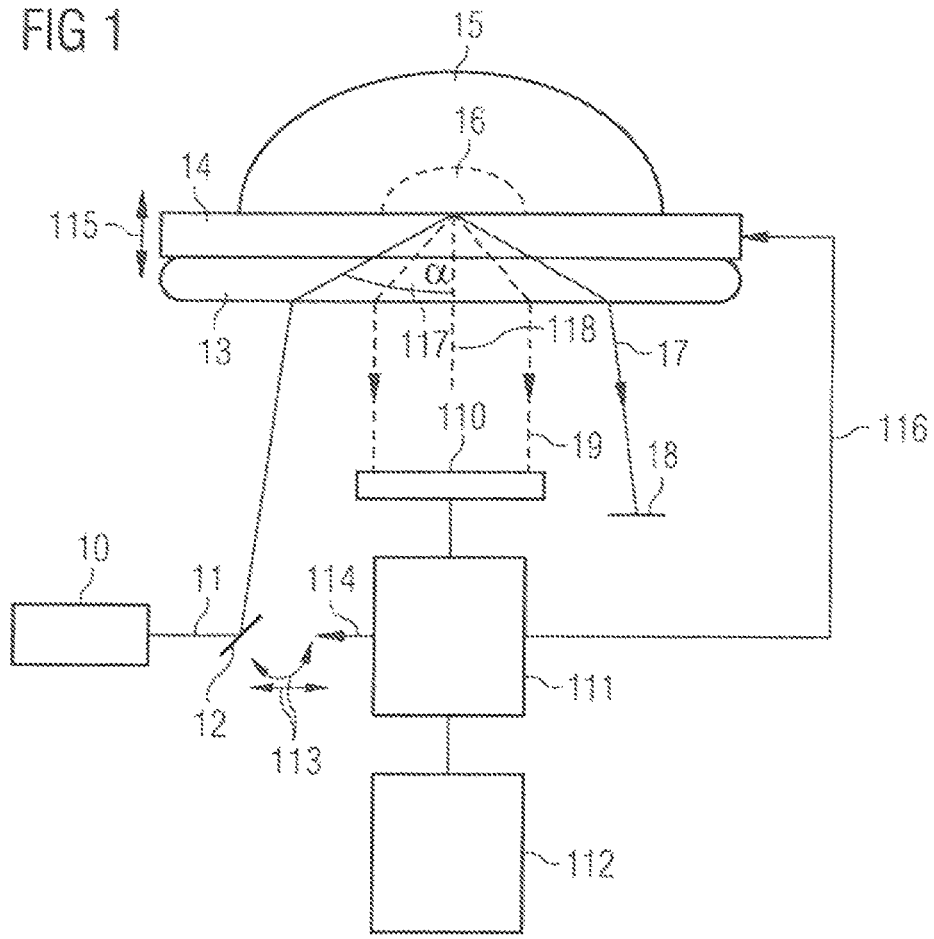
FIG. 1 is a schematic diagram of an apparatus according to an embodiment.

In FIG. 1 a TIRF microscopy apparatus according to an embodiment is schematically shown. It is to be noted that FIG. 1 is to be regarded as being schematic only and serves for illustrating some features of some embodiments. However, additional elements, in particular lenses, mirrors or other optical elements which are used in conventional TIRF microscopy arrangements may also be used in the embodiment of FIG. 1 without being explicitly shown and described.

In the embodiment of FIG. 1 a light source 10, for example a laser light source, generates an excitation light beam 11. Excitation light beam 11 is guided to a sample arrangement 13-15 via a mirror 12. Sample arrangement 13-15 in particular comprises a slide 14 made of glass or other material which is transparent to excitation light beam 11 and to light to be detected from the sample. On a first side of slide 14 a sample 15, for example a suspension with particles to be examined, is provided. On a second side opposing to the first side, the second side facing light source 10, an oil immersion layer 13 is provided. Excitation light beam 11 is refracted at an interface between the surrounding medium (for example air) and oil immersion layer 13 and then impinges on an interface between slide 14 and sample 15 with an angle of incidence $\alpha$ 117. In the embodiment shown, the indices of refraction of oil immersion layer 13 and slide 14 are chosen such that at the interface between oil immersion layer 13 and slide 14 no or only a negligible refraction of excitation light beam 11 takes place.

Excitation light beam 11 is reflected at the interface between slide 14 and sample 15 and, as reflected light beam 17, reaches a light trap 18, which absorbs reflected light beam 17. In other embodiments, reflected light beam 17 may be analysed by corresponding devices if this is helpful for a respective application.

When angle of incidence 117 of excitation light beam 11 at the interface between slide 14 and sample 15 exceeds the critical angle of total reflection for this interface, excitation light beam 11 is totally reflected, and in sample 15 a so-called evanescent field which is exponentially decaying is formed, which is schematically shown in dashed lines in FIG. 1 and provided with reference numeral 16. The critical angle of total reflection depends in particular on the index of refraction of slide 14 and on index of refraction of sample 15. Evanescent field 16 typically has an extension in the order of 100 nm in the direction perpendicular to the above mentioned interface (in the following, this direction is also referred to as z-direction), such that in this manner a high spatial resolution in the z-direction may be obtained. The z-direction therefore corresponds to the direction of perpendicular 118 in FIG. 1.

Excitation light beam 11 may excite fluorescence in sample 15 or parts of sample 15. Corresponding fluorescence light 19 originates from the sample and is detected in the embodiment of FIG. 1 via an image sensor 110, for example a CCD-sensor (Charged Coupled Device) or a CMOS-sensor (Complementary Metal Oxide Semiconductor), this image sensor 110 capturing a fluorescence image of the sample or part thereof, which corresponds to a spatially resolved detection. To this end, an imaging optic (not shown in FIG. 1) which images the sample onto image sensor 110, and/or a corresponding filter arrangement which cancels light in wavelength ranges which do not correspond to the fluorescence to be detected may be provided.

The information captured by image sensor 110 is processed in a processing arrangement 111, for example analysed to determine the critical angle of total reflection as will be described in the following in more detail. Processing arrangement 111 may for example be implemented by programming a processor device with one or more processors, for example a computer, correspondingly. Furthermore, an input/output arrangement 112 is provided via which information may be output to a user, for example via a monitor or other kind of display, and/or data may be input by the user.

In the embodiment shown, mirror 12 is both pivotable as well as movable in a direction parallel to the above-mentioned interface as indicated by arrows 113, to be able to vary angle of incidence 117. Mirror 12 constitutes merely one possible example for a device to change the angle of incidence, and other implementations are also possible. For example, a mirror used may only be movable in a linear direction, and, additionally, a curved mirror, for example a hyperbolic mirror, may be provided. In this case, for example via a linear translation movement of the mirror different points of the curved mirror are illuminated and, thus, the excitation light beam is reflected to the interface between slide 14 and sample 15 by the reflected mirror under different angles, therefore varying in angle of incidence 117.

It is to be noted that in the example of FIG. 1 via the translation movement of mirror 12 parallel to the interface, a change of the location at which excitation light beam 11 falls on the interface caused by a pivoting of mirror 12 may be compensated.

As indicated by an arrow 114, the movement of mirror 12 or another device for changing the angle of incidence may be controlled by processing arrangement 111. In other embodiments the control of mirror 12 or another device may also be performed manually, and processing arrangement 11 is such cases may, for example, instruct a user via input/output arrangement 112 to change the angle of incidence accordingly.

Additionally, in the embodiment of FIG. 1 slide 14 and therefore sample arrangement 13, 14, 15 may be displaced as indicated by an arrow 115 in the z-direction. Through this, an image plane in which the fluorescence is detected by image sensor 110, i.e. an area from which a focused image of the sample is present on the image sensor (depth of field of the imaging) may be moved in z-direction. As an alternative, in some embodiments also image sensor 110 may be movable in z-direction, or an imaging optic (not shown in FIG. 1) between image sensor 110 and sample 15 may be changed accordingly to change the image plane, i.e., the plane where the image is captured, of image sensor 110.

Also this movement or displacement may be controlled by processing arrangement 111 as indicated by an arrow 116. In other embodiments, also in this case the adjustment may be performed manually by a user, the processing arrangement 111, for example, giving instructions to change the position of slide 14 in z-direction to the user via input/output arrangement 112.

To determine the critical angle of total reflection, the apparatus of FIG. 1 is configured to vary angle of incidence 117 automatically or interactively using a user and to determine the critical angle of total reflection through analysis of images captured by image sensor 110 at the different angles of incidence 117. Optionally, additionally the image plane may be changed, for example by moving slide 14 in z-direction as explained above, and images from different image planes additionally may be used for determining the critical angle of total reflection. In particular, a contrast of the images may be evaluated, information at different areas of the images may be evaluated, and/or information for different image planes may be compared. Details of implementation examples will be explained later in more detail.

Figure 2:
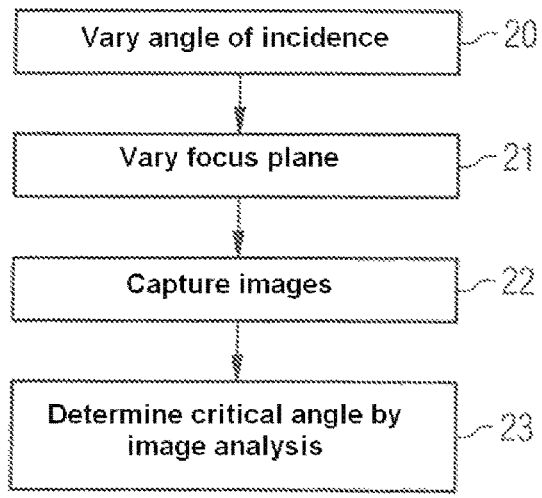
FIG. 2 is a flow-chart of a method according to an embodiment.

In FIG. 2, a corresponding method is shown which may, for example, be implemented in the apparatus of FIG. 1, but which also may be implemented independently therefrom. At 20, an angle of incidence of an excitation light beam, i.e., an illumination angle, on an interface to a sample is varied. When changing the angle of incidence in an embodiment, the directional vector and/or a location where the light beam illuminates the sample is kept as constant as possible. Optionally, at 21 additionally, an imaging plane of an image detection is varied. At 22, the actions at 22 being performed for each angle of incidence and for each image plane of 20 and 21 in some embodiments, corresponding images are captured. At 23, a critical angle of total reflection is determined by analyzing the captured images, for example, by analyzing an image contrast.

Various possibilities for determining the critical angle will now be explained with reference to FIGS. 3 to 7.

Figure 3:
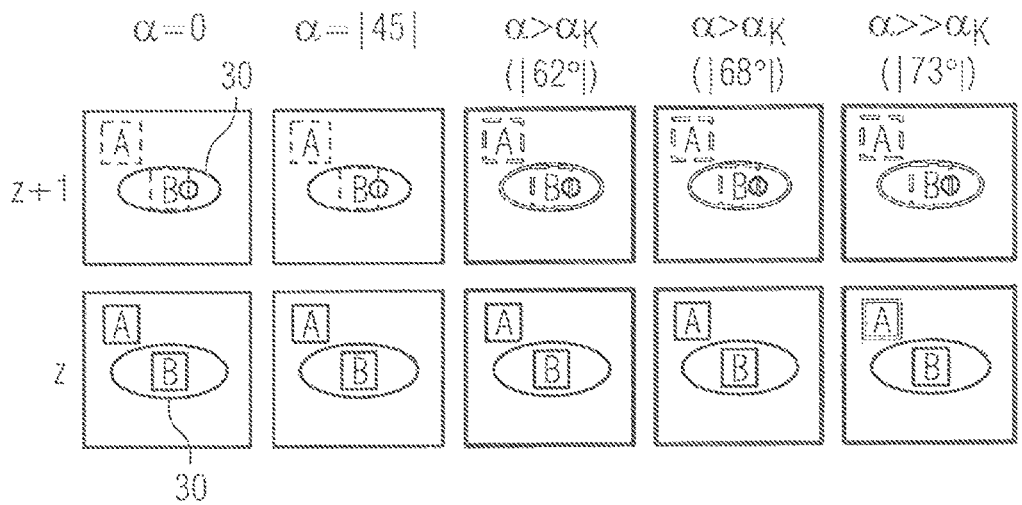
FIG. 3 shows schematic sample images for illustrating an embodiment.
Figure 4:
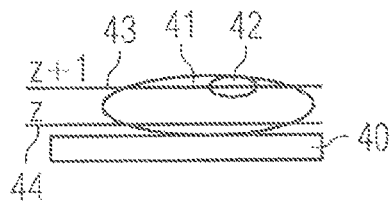
FIG. 4 shows a part of an apparatus according to an embodiment for illustrating an image capturing in different image planes in some embodiments.

In FIG. 3 schematic sample images which are captured by an image sensor like image sensor 110 of FIG. 1 are shown. In FIG. 4 for illustration purposes a corresponding sample with an image plane z 44 and an image plane z+1 43 is shown. In FIG. 4, 40 indicates a slide on which a sample 41 with an object 42 which is present only in image plane 43 is provided.

The distance between image planes 43, 44 is chosen such that when total reflection is present the evanescent field does not reach to image plane 43, i.e., a depth of field when capturing image plane 43 does not include the evanescent field. This causes a different behaviour for the two image planes as will now be explained.

The distance between image planes 43 and 44 is therefore in embodiments, for example, chosen such that it is greater than the penetration depth of the evanescent field, such that image plane 43 is outside the evanescent field.

In the upper row of FIG. 3 images from image plane z+1, i.e., image plane 43 of FIG. 4, are schematically shown, and in the lower row images of image plane z, i.e., image plane 44, are shown. Reference numeral 30 in FIG. 3 denotes where, when the critical angle of total reflection is exceeded, the evanescent field is present within sample 41 of FIG. 3.

In the columns of FIG. 3, images for different angles of incidence α are shown, namely α=0, α=45°, α=62°, α=68° and α=73°. The critical angle of total reflection $\alpha_K$ in this example is slightly below 62°.

To determine the critical angle of total reflection in the example shown, two areas are evaluated which are designated A and B in FIG. 3, area B being within area 30 and area A being outside area 30.

In the images shown in FIG. 3, different light intensities, for example fluorescence intensity detected by the respective image sensor, in areas A and B are represented by different types of lines surrounding the letters "A" and "B".

For angles α smaller than the critical angle of total reflection, in FIG. 3 the complete image except element 42 appears light. This corresponds to the first two columns in FIG. 3. When the critical angle is exceeded in image plane z+1, the complete image is dark. This is caused by the fact that in this case the excitation light beam is total reflected and in image plane z+1 no evanescent field is present, such that here no excitation takes place and therefore no light is emitted by the sample, in particular no fluorescence light.

In image plane 44, i.e., in image plane z, when exceeding the critical angle (last column in FIG. 3) the signal outside of area 30 becomes weaker, whereas the signal in area 30 increases slightly and then decays slowly. This is caused by the fact that, when exceeding the critical angle basically only in area 30 an evanescent field is present which may cause an excitation. With increasing angle of incidence this evanescent field becomes weaker, and therefore the intensity in area 30 decreases.

Figure 5:
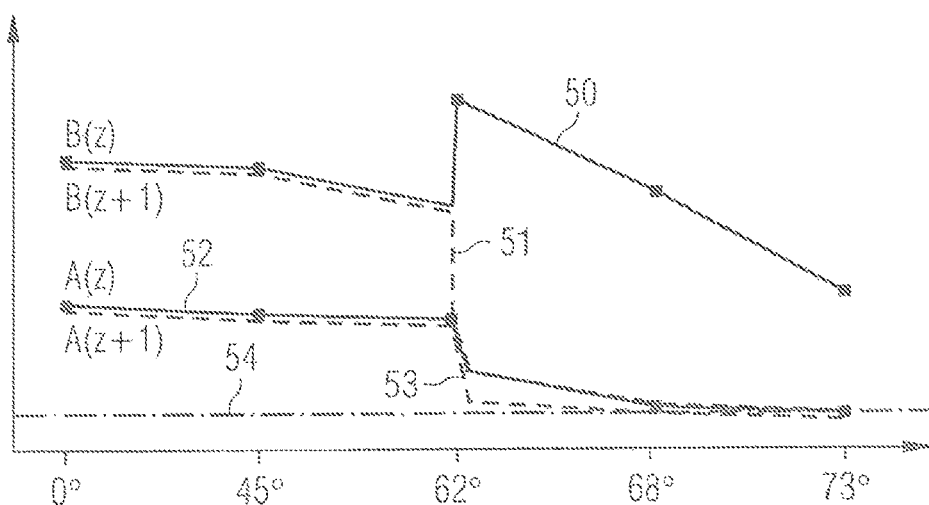
FIG. 5 shows graphs for illustrating a determination of a critical angle in some embodiments.

These results are graphically shown in FIG. 5. A curve 50 shows a development of a densiometric mean value of the intensity in area B for image plane z, a curve 51 shows the development for area B in image plane z+1, a curve 52 shows the development for area A in image plane z, and curve 53 shows the development for area A in image plane z+1. A line 54 indicates dark noise of the image sensor used.

As can be seen, all curves show a strong change at the critical angle of total reflection, curve 50 increasing to then decrease again, whereas all other curves decrease strongly at the critical angle.

Figure 6:
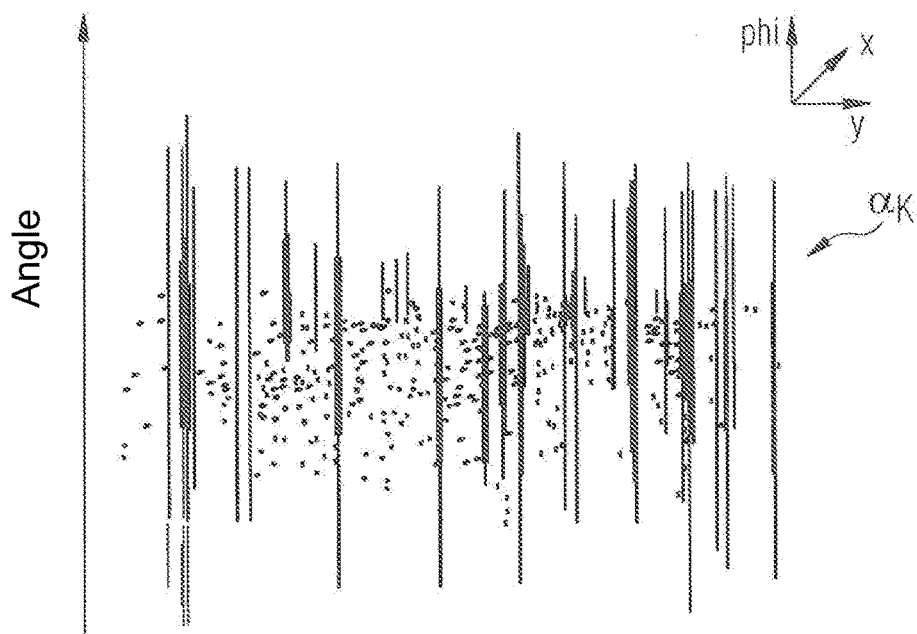
FIGS. 6 and 7 show examples of measurements in two different image areas.
Figure 7:
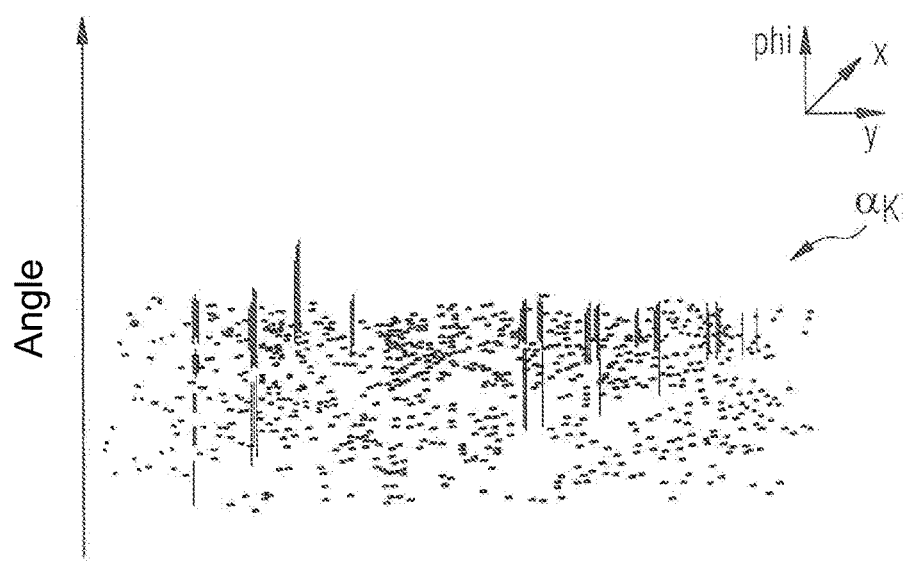

For further illustration, in FIGS. 6 and 7 further measurements are shown, the measurements of FIG. 6 having been measured in image plane z, whereas the measurement of FIG. 7 have been measured in image plane z+1, i.e. outside the evanescent field. The lines shown an intensity distribution in y-direction, i.e., in the image plane of the image sensors used, the dots between the lines corresponding to background signals. The signal, represented by the lines, in the example shown is generated by fluorescence beads of 1.2 μm diameter, whereas the background signal may, for example, be caused by fluorescein or fluorescent markers in the liquid in which the beads are provided. As can be seen in FIG. 6, when exceeding the critical angle (marked with $\alpha_K$) the background signal strongly decreases, whereas the signal from the beads remains. In contrast thereto, in FIG. 7, when exceeding the critical angle, both background and the signal itself decrease strongly.

From the above explained properties of the recorded images with varying image plane and/or varying angles of incidence, various possibilities for determining the critical angle result. In a simple case, simply the bending or the step in the various graphs of FIG. 5 may be detected. In another embodiments, image intensities $I_z/I_{z+1}$ along one or more line profiles or based on complete images are evaluated, I indicating the intensity, $I_z$ the intensity of a line profile or the complete image for image plane z, and $I_{z+1}$ the corresponding quantity for image plane z+1. Through the strong decrease when exceeding the critical angle in the image plane z+1 together with the constant or increasing behavior in the image plane z, an exceeding of the critical angle causes a strong increase of this ratio, which may be detected. Additionally or alternatively, in some embodiments, in order to reduce a sample dependence (for example, to reduce an influence of sample bleaching) in a first step a ratio $I_a$ to $I_{a+1}$ may be determined, I being the fluorescence intensity of an area of interest or of the complete image and a being an index of a measurement for a specific angle of incidence, i.e., a+1 denotes the measurement with the next greater angle of incidence compared to measurement a. This may be performed, for example, in image plane z. Also, here the ratio changes when the critical angle is exceeded. Finally, it is possible, for example for fine-tuning, to evaluate two areas in an image, for example an area where a sample to be measured is located and an area the signal of which may suppressed by illumination with an angle of incidence above the critical angle, for examples areas B and A in FIG. 3, for example the complete areas or line profiles in the respective areas. Also, an out-of-focus area may be selected for area A, i.e., the area which is not of interest for a later measurement. When here the intensity ratios are formed for image plane z when the critical angle is exceeded, a change by a specific factor occurs. For example, a threshold value may be selected, and when this factor exceeds the threshold value from one angle of incidence to the next, this corresponds to detection of the critical angle. The threshold value may, for example, be determined by a user or may be set to a typical value, for example a value of 10.

Thus, various possibilities have been provided how the critical angle may be determined on the basis of contrast information of images to be analyzed, for example on the basis of intensity ratios.

The above methods may also be combined with each other, for example to verify a result obtained by one of the methods with another one of the methods or techniques.

The above apparatuses and methods are merely to be seen as examples. For example, in the apparatus of FIG. 1, fluorescence light originating from sample 15 is detected on the same side from which also excitation light beam 11 is provided. In other embodiments, fluorescence light may additionally or alternatively be detected on the opposite side. Furthermore, the present invention is not limited to the detection of fluorescence light, but, generally, light emitted (originating) from the sample in response to the excitation light beam, for example Raman-scattered light, may be detected.

Therefore, the application is not limited to the embodiments shown.

What is claimed is:

1. A method for determining a critical angle of total reflection, comprising:
   illuminating a sample with an excitation light beam of a light source;
   using an image capturing sensor, capturing fluorescence images at a plurality of different angles of incidence of the excitation light beam, wherein each of the fluorescence images comprises a first image area including an object to be examined and a second image area outside the object; and
   using a processor, determining a critical angle of total reflection at an interface of the sample based upon an analysis of the fluorescence images, wherein said analysis comprises:
      forming for each fluorescence image an intensity ratio between a first fluorescence intensity in the first image area of one of the fluorescence images and a second fluorescence intensity in the second image area of said one of the fluorescence images, wherein said ratio being formed by dividing one of the first and second fluorescence intensities by the other of the first and second fluorescence intensities; and
      evaluating the intensity ratios for the plurality of angles of incidence.

2. The method according to claim 1, wherein the step of determining the critical angle comprises evaluating ratios of a light intensity in a predetermined area of images with adjacent angles of incidence, each ratio being formed by dividing an intensity at one angle of incidence by an intensity at an adjacent angle of incidence.

3. The method according to claim 1, wherein the step of capturing the images comprises capturing images for at least two different image planes.

4. The method according to claim 3, wherein a distance between the at least two image planes is greater than a penetration depth of an evanescent field when the angle of incidence exceeds the critical angle.

5. The method according to claim 3, wherein the step of determining the critical angle comprises a comparing of areas in images with the same angle of incidence in different image planes.

6. The method according to claim 1, wherein the step of determining the critical angle comprises comparing an intensity ratio based upon the plurality of images with a threshold value.

7. The method according to claim 1, wherein the plurality of angles of incidence is set automatically.

8. An apparatus for determining a critical angle of total reflection at an interface of a sample, comprising:
   a light source operable to illuminate a sample with an angle of incidence;
   an image capturing sensor operable to capture fluorescence images of the sample, wherein each of the fluorescence images comprises a first image area including an object to be examined and a second image area outside the object; and
   a processor operable to determine a critical angle of total reflection at an interface of the sample based upon an analysis of the fluorescence images captured at a plurality of different angles of incidence, wherein said analysis comprises:
      forming for each fluorescence image an intensity ratio between a first fluorescence intensity in the first image area of one of the fluorescence images and a second fluorescence intensity in the second image area of said one of the fluorescence images, wherein said ratio being formed by dividing one of the first and second fluorescence intensities by the other of the first and second fluorescence intensities; and
      evaluating the intensity ratios for the plurality of angles of incidence.

9. The apparatus according to claim 8, wherein the image capturing sensor comprises one of a CCD-sensor and a CMOS-sensor.

10. The apparatus according to claim 8, wherein the processor is configured to determine the critical angle based upon contrast information of the images.

11. The apparatus according to claim 8, further comprising a device configured to change the angle of incidence.

12. The apparatus according to claim 8, further comprising an imaging device operable to change an image plane of the image capturing sensor.

13. The apparatus according to claim 12, wherein the processor is configured to determine the critical angle based upon an analysis of images captured at different image planes.

14. A method for determining a critical angle of total reflection, comprising:
   illuminating a sample with an excitation light beam of a light source;

using an image capturing sensor, capturing fluorescence images of at least part of the sample at a plurality of different angles of incidence of the excitation light beam and for at least a first image plane and a second image plane different from the first image plane, wherein each image plane comprises a first image area including an object to be examined and a second image area outside the object; and using a processor, determining a critical angle of total reflection at an interface of the sample based upon an analysis of the fluorescence images, wherein said analysis comprises:

forming for each image plane an intensity ratio between a first fluorescence intensity in the first image area of one of the image planes and a second fluorescence intensity in the second image area of said one of the image planes, wherein said ratio being formed by dividing one of the first and second fluorescence intensities by the other of the first and second fluorescence intensities; and evaluating the intensity ratios for the plurality of angles of incidence.

15. The method according to claim 14, wherein a distance between the first and second image planes is greater than a penetration depth of an evanescent field when the angle of incidence exceeds the critical angle.

16. The method according to claim 14, wherein the step of determining the critical angle comprises a comparing of areas in images with the same angle of incidence in different image planes.

17. The method according to claim 1, wherein evaluating intensity ratios comprises detecting a change of the ratio at or near the critical angle based on the first intensity behaving differently from the second intensity when crossing the critical angle.

18. The method according to claim 14, wherein the step of determining the critical angle is based on one of the first and second fluorescence intensities increasing or staying constant while the other one of the first and second fluorescence intensities is decreasing when increasing the angle of incidence across the critical angle and detecting an increase of the intensity ratio when crossing the critical angle.

19. The apparatus according to claim 8, wherein the evaluation of light intensity ratios comprises:

for each fluorescence image:
    detecting in the first image area the first fluorescence intensity;
    detecting in the second image area the second fluorescence intensity; and
    forming a respective intensity ratio between the first fluorescence intensity and the second fluorescence intensity; and evaluating the respective intensity ratios for the plurality of angles of incidence.

20. The apparatus according to claim 19, wherein each respective intensity ratio is formed by dividing one of the first and second fluorescence intensities by the other of the first and second fluorescence intensities.

21. The apparatus according to claim 8, wherein the first image area is spaced apart from the second image area.

22. The method according to claim 14, wherein the step of capturing fluorescence images comprises:

capturing a first fluorescence image in which a focus of the image capturing sensor is in the first image plane; and capturing a second fluorescence image in which the focus of the image capturing sensor is in the second image plane.

* * * * *